US012784898B2

(12) United States Patent
Matsumura et al.

(10) Patent No.: US 12,784,898 B2
(45) Date of Patent: Nov. 3, 2026

(54) MEDICAL INFORMATION PROCESSING APPARATUS, METHOD, AND STORAGE MEDIUM

(71) Applicant: Canon Kabushiki Kaisha, Tokyo (JP)

(72) Inventors: Yuka Matsumura, Shioya (JP); Minoru Nakatsugawa, Yokohama (JP); Kazumasa Noro, Shioya (JP); Yusuke Kano, Edinburgh (GB); Longxun Piao, Nasushiobara (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 18/678,713

(22) Filed: May 30, 2024

(65) Prior Publication Data

US 2024/0404680 A1 Dec. 5, 2024

(30) Foreign Application Priority Data

May 30, 2023 (JP) ................................ 2023-088421

(51) Int. Cl.
*G16H 40/00* (2018.01)
*G16H 10/60* (2018.01)
*G16H 50/20* (2018.01)
*G16H 50/70* (2018.01)

(52) U.S. Cl.
CPC ............ *G16H 40/00* (2018.01); *G16H 10/60* (2018.01); *G16H 50/20* (2018.01); *G16H 50/70* (2018.01)

(58) Field of Classification Search
None
See application file for complete search history.

(56) References Cited

U.S. PATENT DOCUMENTS

| | | | | |
|---|---|---|---|---|
| 2018/0042558 | A1* | 2/2018 | Cabrera, Jr. | G06F 3/0488 |
| 2021/0125731 | A1* | 4/2021 | Lefkofsky | G16H 20/10 |
| 2021/0343415 | A1* | 11/2021 | Allen | G16H 40/20 |
| 2022/0253729 | A1* | 8/2022 | Vashist | G06N 5/04 |

FOREIGN PATENT DOCUMENTS

JP 2020-30465 A 2/2020

OTHER PUBLICATIONS

Chen et al. ("Mapping of diseases from clinical medicine research-a visualization study." Scientometrics 125 (2020): 171-185) (Year: 2020).*

* cited by examiner

*Primary Examiner* — Christopher B Tokarczyk
(74) *Attorney, Agent, or Firm* — Oblon, McClelland, Maier & Neustadt, L.L.P.

(57) ABSTRACT

A medical information processing apparatus according to an embodiment includes processing circuitry. The processing circuitry identifies a medical concept relating to a patient. The processing circuitry determines an evaluation parameter relating to the medical concept. The processing circuitry acquires chief complaint data of the patient and medical knowledge relating to the medical concept. The processing circuitry maps the first range based on the chief complaint data and the second range based on the medical knowledge on a space based on the evaluation parameter.

14 Claims, 14 Drawing Sheets

| CANDIDATE OF DISEASE/ADVERSE EVENT | IMPORTANCE | OUTPATIENT CONSULTATION, LITERATURE INFORMATION |
|---|---|---|
| SPINAL CORD PARALYSIS | 80 | BONE METASTASIS GUIDELINE |
| PAIN DUE TO BONE METASTASIS | 70 | PALLIATIVE CARE GUIDELINE |
| DIABETIC NEUROPATHY | 20 | DIABETES GUIDELINE |
| | | |
| | | |

| CANDIDATE OF DISEASE/ADVERSE EVENT | PREDICTION PROBABILITY |
| --- | --- |
| PERIPHERAL NEUROPATHY | 50 |
| SPINAL CORD PARALYSIS | 30 |
| ATELECTASIS PNEUMONIA | 20 |
| | |
| | |

MEDICAL INFORMATION PROCESSING APPARATUS, METHOD, AND STORAGE MEDIUM

CROSS-REFERENCE TO RELATED APPLICATIONS

This application is based upon and claims the benefit of priority from Japanese Patent Application No. 2023-088421, filed on May 30, 2023; the entire contents of which are incorporated herein by reference.

FIELD

Embodiments described herein relate generally to a medical information processing apparatus, a method, and a storage medium.

BACKGROUND

Because symptoms reported by a patient and the like are subjective evaluations of the patient, there can be variations in location, severity, type of symptoms, and the like. On the other hand, symptoms described in guidelines or literature are abstract, and that can make it difficult to determine whether they correspond to the chief complaint of the patient. However, if a symptom is overlooked, it can lead to overlooking of a serious disease. Therefore, physicians are required to conduct interviews to resolve ambiguities in the chief complaint of the patient within a short time.

DETAILED DESCRIPTION

A medical information processing apparatus according to an embodiment includes processing circuitry. The processing circuitry is configured to identify a medical concept about a patient. The processing circuitry is configured to determine an evaluation parameter relating to the medical concept. The processing circuitry is configured to acquire chief complaint data of the patient, and a medical knowledge relating to the medical concept. The processing circuitry is configured to map a first range based on the chief complaint and a second range based on the medical knowledge on a space based on the evaluation parameter.

Hereinafter, embodiments of a medical information processing apparatus, a method, and a storage medium will be explained in detail with reference to the drawings. The medical information processing apparatus, the method, and the storage medium according to the present application are not limited to the embodiments described below.

First Embodiment

Figure 1:
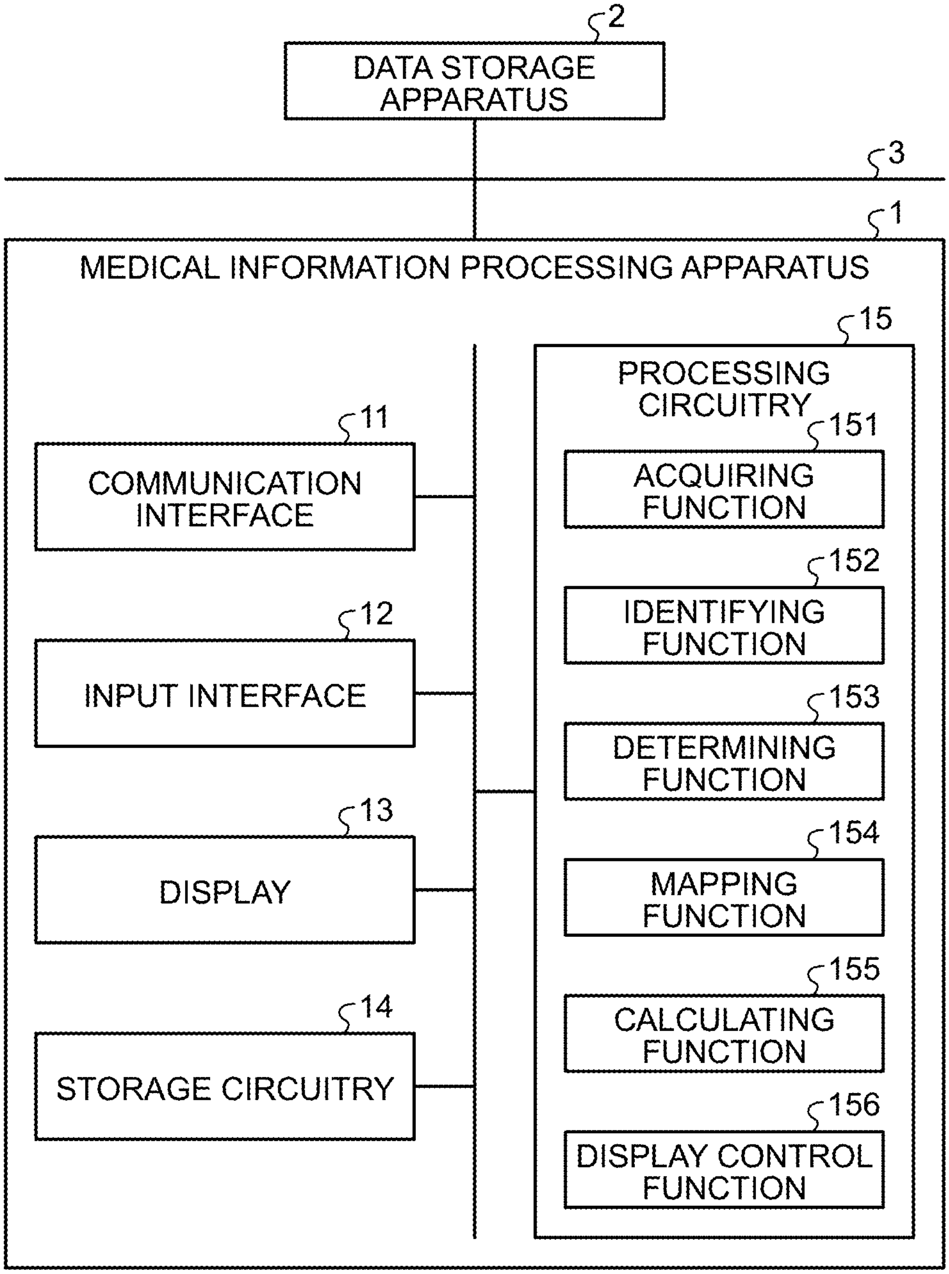
FIG. 1 is a block diagram illustrating a medical information processing apparatus according to a first embodiment.

FIG. 1 is a block diagram illustrating a medical information processing apparatus according to the first embodiment. For example, as illustrated in FIG. 1, the medical information processing apparatus 1 according to the present embodiment is connected to a data storage apparatus 2 through a network 3 in a communication-enabled manner. The network 3 includes, for example, an in-hospital local area network (LAN) installed in a hospital and a wide area network (WAN). To the network 3 illustrated in FIG. 1, only the medical information processing apparatus 1 and the data storage apparatus 2 are connected, but various other devices and systems are connected in an actual situation.

The data storage apparatus 2 archives information, such as medical information (clinical data) of a patient and various guidelines. Specifically, the data storage apparatus 2 receives data of medical information from various devices and systems connected to the network 3 (raw data, medical images, analysis results, reports, and the like), and stores the received data of medical information in its internal storage circuitry to archive it. Moreover, the data storage apparatus 2 stores, according to operations for archiving information, such as guidelines and literature, data of the information in its internal storage circuitry to archive it. For example, the data storage apparatus 2 is implemented by a picture archiving and communication system (PACS), a hospital information system (HIS), a radiology information system (RIS), or the like.

The medical information processing apparatus 1 is an apparatus operated by physicians working in a hospital, and performs various kinds of processing to improve the efficiency of diagnosis by the physicians. Specifically, the medical information processing apparatus 1 improves the efficiency of diagnosis by identifying ambiguities to be resolved when diagnosing a patient. As described above, because symptoms reported by a patient and the like are subjective evaluations of the patient, there can be variations in location, severity, type of symptoms, and the like, and can contain ambiguities. Therefore, the medical information processing apparatus 1 improves the efficiency of interviews by identifying ambiguities to be resolved out of ambiguities included in a chief complaint of the patient, to improve the efficiency of diagnosis. Moreover, by resolving ambiguities included in the chief complaint of the patient, necessary examinations and treatments are performed appropriately, and it enables to prevent overlooking of signs of a serious disease or an adverse event. For example, the medical information processing apparatus 1 is implemented by a computer device, such as a personal computer (PC), a work station, and a server.

The medical information processing apparatus 1 according to the present embodiment includes, as illustrated in FIG. 1, a communication interface 11, an input interface 12, a display 13, storage circuitry 14, and processing circuitry 15.

The communication interface 11 controls transmission and of various kinds of data communicated with respective devices connected through the network 3 and communications. Specifically, the communication interface 11 is connected to the processing circuitry 15, and transmits data received from the respective devices on the network 3 or transmits data received from the processing circuitry 15 to the respective devices on the network 3. For example, the communication interface 11 is implemented by a network card, a network adaptor, a network interface controller (NIC), or the like.

The input interface 12 accepts an input operation of various kinds of instructions from an operator and various kinds of information. Specifically, the input interface 12 is connected to the processing circuitry 15, and converts the input operation received from the operator into an electrical signal, to transmit to the processing circuitry 15. For example, the input interface 12 is implemented by a trackball, a switch button, a mouse, a keyboard, a touch pad with which an input operation is performed by touching an operating surface, a touch screen in which a display screen and a touch pad are integrated, a non-contact input interface using an optical sensor, a sound input interface, and the like. In the present specification, the input interface 12 is not limited to those including a physical operating part, such as a mouse and a keyboard. For example, a processing circuit of an electrical signal that receives an electrical signal corresponding to an input operation from an external input device arranged separately from the device and that outputs this electrical signal to the control circuit is also included in examples of the input interface 12.

The display 13 displays various kinds of information and various kinds of data. Specifically, the display 13 is connected to the processing circuitry 15, and displays various kinds of information and various kinds of data received from the processing circuitry 15. For example, the display 13 is implemented by a liquid crystal display, a cathode ray tube (CRT) display, a touch panel, and the like.

The storage circuitry 14 stores various kinds of data and various kinds of programs. Specifically, the storage circuitry 14 is connected to the processing circuitry 15, and stores data received from the processing circuitry 15, or reads stored data to transmit to the processing circuitry 15. For example, the storage circuitry 14 is implemented by a semiconductor memory device, such as a read only memory (ROM), a random access memory (RAM), and a flash memory, a hard disk, an optical disk, or the like. The storage circuitry 14 may be implemented by a cloud computer that is connected to the medical information processing apparatus 1 through the network 3.

The processing circuitry 15 controls the entire medical information processing apparatus 1. Specifically, the processing circuitry 15 performs various kinds of processing to identify ambiguities to be resolved. For example, the processing circuitry 15 controls communication of data with devices on the network 3, storage of data to the storage circuitry 14, and various processing using the data.

For example, as illustrated in FIG. 1, in the present invention, the processing circuitry 15 of the medical information processing apparatus 1 implements an acquiring function 151, an identifying function 152, a determining function 153, a mapping function 154, a calculating function 155, and a display control function 156. The processing circuitry 15 is one example of processing circuitry.

The acquiring function 151 acquires various data from a device connected on the network 3. Specifically, the acquiring function 151 acquires information, such as medical information of a patient and various guidelines, from the data storage apparatus 2. The acquiring function 151 extracts various kinds of information from the information such as the medical information of the patient and the guidelines, based on a medical concept relating to the patient. For example, the acquiring function 151 acquires chief complaint data of the patient and a medical knowledge relating to the medical concept. Processing performed by the acquiring function 151 will be described in detail later.

The identifying function 152 identifies a medical concept relating to a patient. Specifically, the identifying function 152 identifies information about a disease of the patient. Processing performed by the identifying function 152 will be described in detail later.

The determining function 153 determines an evaluation parameter relating to the medical concept. Specifically, the determining function 153 determines an evaluation parameter that is a parameter relating to the medical concept and containing ambiguities. That is, the determining function 153 determines a parameter that contains ambiguities in evaluations as the evaluation parameter, out of parameters to evaluate the medical concept of the patient. Processing performed by the determining function 153 will be described in detail later.

The mapping function 154 maps a first range based on a chief complaint and a second range based on a medical knowledge on a space based on the evaluation parameters. Specifically, the mapping function 154 determines the first range on the space based on the evaluation parameter based on an evaluation relating to the medical concept that is included in the chief complaint, and determines the second range on the space based on the evaluation parameter based on evaluations relating to the medical concept included in the medical knowledge. Processing performed by the mapping function 154 will be described in detail later.

The calculating function 155 calculates a relevance between chief complaint data and the medical knowledge based on the first range and the second range. Processing performed by the calculating function 155 will be described in detail later.

The display control function 156 controls to display information based on the relevance. Processing performed by the display control function 156 will be described in detail later.

The processing circuitry 15 is implemented by, for example, a processor. In this case, the respective processing functions described above are stored in the storage circuitry 14 in a form of a computer-executable program. The processing circuitry 15 reads out the respective programs stored in the storage circuitry 14, and the implements the functions corresponding to the respective programs. In other words, the processing circuitry 15 is to have the respective functions indicated in FIG. 1 in a state in which the respective programs are loaded.

The processing circuitry 15 may be constituted by combining multiple independent processors, to implement the respective processing functions by the respective processors executing the programs. Moreover, the respective processing functions included in the processing circuitry 15 may be implemented by a single or multiple processing circuits in an appropriately distributed or integrated manner. Furthermore, the respective processing circuit included in the processing circuitry 15 may be implemented by combination of hardware, such as a circuit, and software. Moreover, an example in which the programs corresponding to the respective processing functions are stored in a single unit of the storage circuitry 14 has been explained herein, but the embodiments are not limited thereto. For example, it may be configured such that the programs corresponding to the respective processing functions are stored in multiple storage circuits in a distributed manner, and are performed by reading the respective programs from the respective storage circuits by the processing circuitry 15. Some of the respective processing functions included in the processing circuitry 15 may be implemented by a cloud computer connected to the medical information processing apparatus 1 through the network 3.

Figure 2:
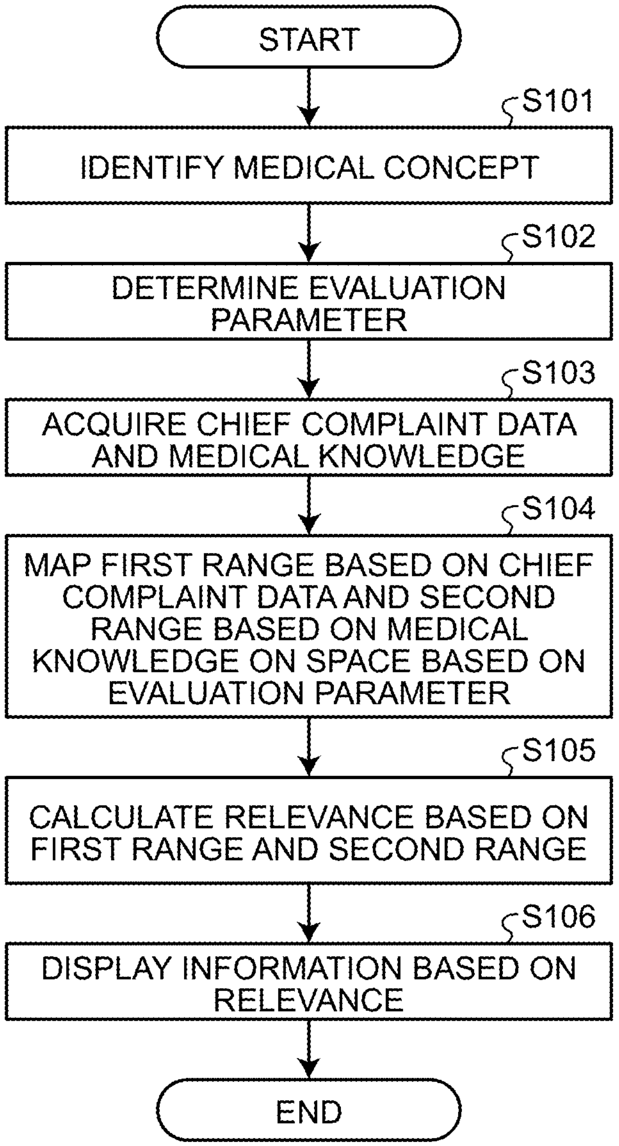
FIG. 2 is a flowchart illustrating an example of processing procedure of the medical information processing apparatus according to the first embodiment.

Next, after a procedure of processing performed by the medical information processing apparatus 1 is explained using FIG. 2, details of the respective processing will be explained. FIG. 2 is a flow chart illustrating an example of the processing procedure of the medical information processing apparatus 1 according to the first embodiment.

For example, as illustrated in FIG. 2, in the present embodiment, the identifying function 152 identifies a medical concept of a patient (step S101). Specifically, the identifying function 152 identifies the medical concept of the patient based on information relating to the patient acquired by the acquiring function 151. This processing is implemented by the processing circuitry 15 reading out a program corresponding to the acquiring function 151 and the identifying function 152 from the storage circuitry 14.

Subsequently, the determining function 153 determines an evaluation parameter relating to the medical concept (step S102). This processing is implemented by the processing circuitry 15 reading out a program corresponding to the determining function 153 from the storage circuitry 14 and executing it.

Subsequently, the acquiring function 151 acquires chief complaint data of the patient and a medical knowledge relating to the medical concept (step S103). This processing is implemented by the processing circuitry 15 reading out a program corresponding to the acquiring function 151 from the storage circuitry 14 and executing it.

Subsequently, the mapping function 154 maps the first range based on the chief complaint data and the second range based on the medical knowledge on a space based on the evaluation parameter (step S104). This processing is implemented by the processing circuitry 15 reading out a program corresponding to the mapping function 154 from the storage circuitry 14 and executing it.

Subsequently, the calculating function 155 calculates a relevance between the chief complaint data and the medical knowledge based on the first range and the second range (step S105). This processing is implemented, for example, by the processing circuitry 15 reading out a program corresponding to the calculating function 155 from the storage circuitry 14 and executing it.

Subsequently, the display control function 156 displays information based on the relevance (step S106). This processing is implemented, for example, by the processing circuitry 15 reading out a program corresponding to the display control function 156 from the storage circuitry 14, and executing it.

Hereinafter, details of the respective processing performed by the medical information processing apparatus 1 will be explained. In the following, a case in which signs of spinal cord paralysis due to bone metastasis is determined in a patient that is undergoing chemotherapy for lung cancer and has a history of numbness in hands and feet due to peripheral neuropathy originated from the chemotherapy will be explained. Specifically, because numbness in hands and feet are caused also by spinal cord paralysis due to bone metastasis, in the present embodiment, an example of supporting diagnosis on whether there are signs of spinal cord paralysis due to bone metastasis based on a chief complaint of the patient will be explained.

Identification Processing of Medical Concept

AS explained at step S101 in FIG. 2, the identifying function 152 identifies a medical concept relating to the patient. The medical concept is information relating to a disease of the patient, and includes, for example, disease name, disease status, treatment method, symptom, side effects, effect (improvement and the like), indicator or score reflecting a patient status, disease subtype, and pathological classification.

The identifying function 152 identifies the medical concept relating to the patient based on diagnosis data of the patient and assessment of a physician. As one example, the identifying function 152 identifies the medical concept of the patient based on a designation by a physician or on actions taken by a physician. Moreover, the identifying function 152 identifies the medical concept of the patient from diagnosis data of the patient by a method using ontology and disease prediction, a rule-based approach targeting guideline information or the like, or a search method utilizing medical terminology. The medical concept may be identified by a combination of diagnosis data of a patient and an assessment of a physician.

Figure 3A:
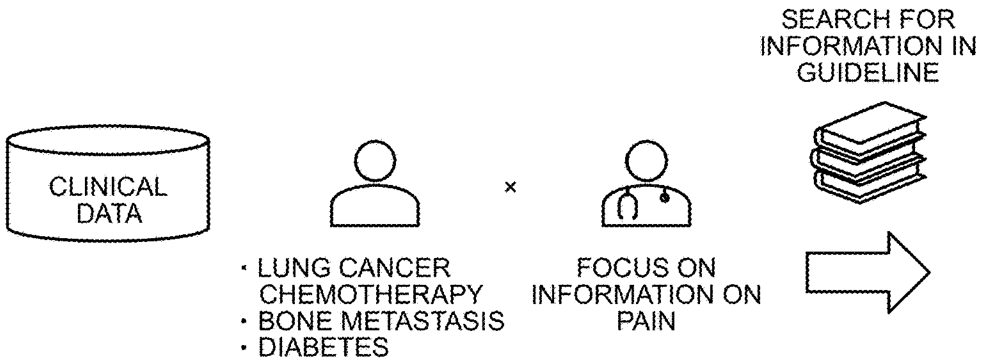
FIG. 3A is a diagram for explaining a specific example of medical concept according to the first embodiment.
Figure 3B:
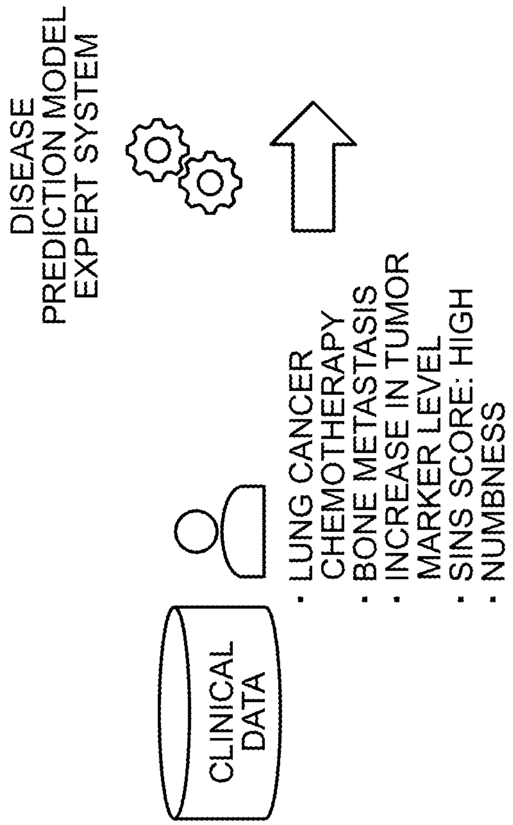
FIG. 3B is a diagram for explaining a specific example of medical concept according to the first embodiment.

FIG. 3A and FIG. 3B are diagrams explaining an example of identification of the medical concept according to the first embodiment. For example, the identifying function 152 identifies, as illustrated in FIG. 3A, the medical concepts "spinal cord paralysis", "pain due to bone metastasis", and "diabetic neuropathy" based on a search for guideline information using "lung cancer chemotherapy", "bone metastasis", and "diabetes" included in the diagnosis data of the patient, and on an action of the physician, "focusing on pain information." As illustrated in FIG. 3A, importance may be assigned to each medical concept. The rules and medical terminologies for searching guideline information are predefined and stored in the storage circuitry 14. That is, the identifying function 152 identifies the medical concept using those information stored in the storage circuitry 14.

Moreover, for example, the identifying function 152 identifies, as illustrated in FIG. 3B, the medical concepts "peripheral neuropathy", "spinal cord paralysis", "atelectasis pneumonia" by using a disease prediction model or an expert system defined by ontology using "lung cancer chemotherapy", "bone metastasis", "increase in tumor marker levels", "SINS score: high", and "numbness" included in the diagnosis data of the patient. As illustrated in FIG. 3B, prediction probability may be assigned to each medical concept. The disease prediction model and the expert system are created in advance and stored in the storage circuitry 14. That is, the identifying function 152 identifies the medical concept by using those stored in the storage circuitry 14.

Note that the examples illustrated in FIG. 3A and FIG. 3B are only example, and other methods may be used to identify the medical concept. For example, the identifying function 152 can identify a single piece of information designated by a physician as the medical concept. Furthermore, the identifying function 152 can further narrow down candidates from multiple medical concepts indicated in FIG. 3A and FIG. 3B based on the importance, the relevance, and the prediction probability. Moreover, when the diagnosis data is used to identify the medical concept, prior to identification of the medical concept, the acquiring function 151 acquires the diagnosis data of a patient to be a subject from the data storage apparatus 2.

Determination Processing of Evaluation Parameter

As explained at step S102 in FIG. 2, the determining function 153 determines the evaluation parameter relating to the medical concept identified by the identifying function 152. Specifically, the determining function 153 determines the evaluation parameter relating to the medical concept identified by the identifying function 152 by rule-based extraction predefined for each medical concept, or by extraction based on language processing. When extracting based on rules predefined for each medical concept, the determining function 153 reads out rules corresponding to the medical concept from among rules stored in the storage circuitry 14 in advance, and determines the evaluation parameter based on the read rules. The rules stored in the storage circuitry 14 are information to which an evaluation parameter is associated for each medical concept. Multiple evaluation parameters may be associated with a medical concept.

Figure 4A:
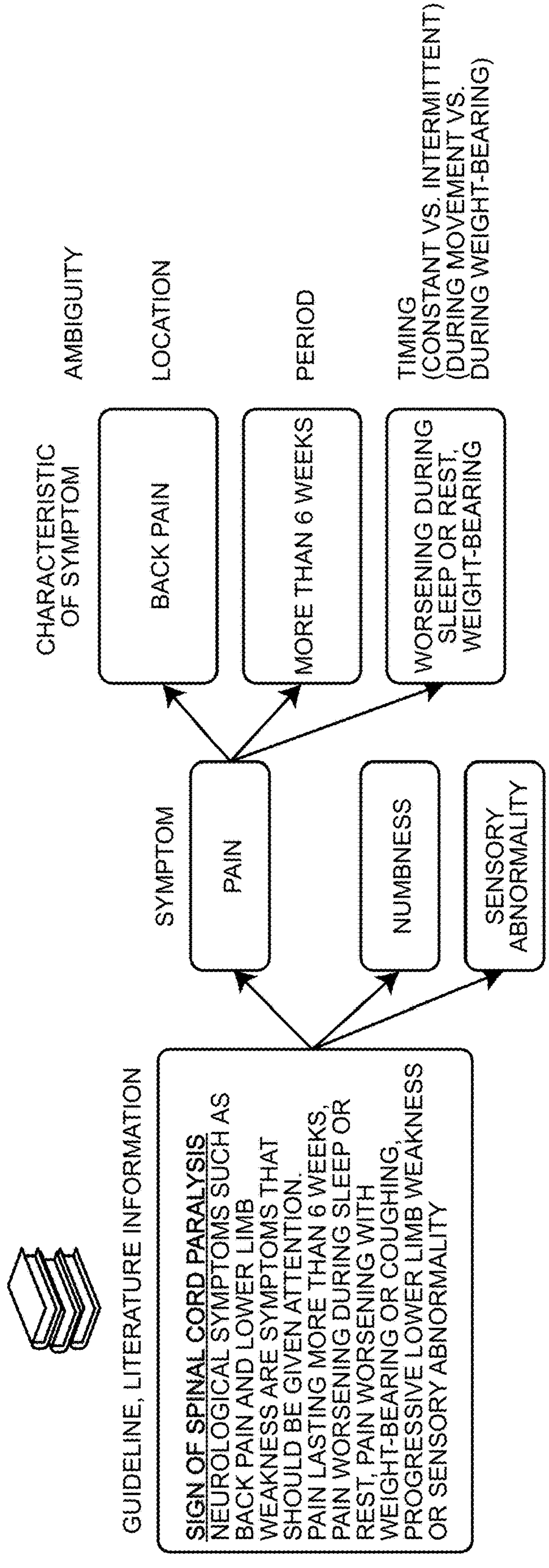
FIG. 4A is a diagram for explaining an example of determination processing of evaluation parameters according to the first embodiment.

FIG. 4A is a diagram for explaining an example of determination processing of the evaluation parameter according to the first embodiment. FIG. 4A illustrates a case in which the evaluation parameter is extracted by a language processing technique from guideline information or information described in literature. As the language processing technique, rule-based methods, dictionaries, ontology utilization, and named entity recognition are applied.

For example, the determining function 153 extracts, as illustrated in FIG. 4A, words indicating symptoms from guidelines and literature information relating to the medical concept, "spinal cord paralysis", such as "pain", "numbness", and "sensory abnormality". Furthermore, the determining function 153 extracts words modifying the extracted symptom (characteristics of the symptom), such as "back pain", "lasting more than 6 weeks", and "exacerbated during sleep, rest, and weight-bearing". The determining function 153 extracts a category of characteristics of the symptom as the evaluation parameter. That is, the determining function 153 determines respective categories, "location", "duration", and "timing" as the evaluation parameters (ambiguities to be narrowed down (ambiguities to be resolved)) for each category as illustrated in FIG. 4A. In FIG. 4A, a case in which multiple kinds of evaluation parameters are determined from a single medical concept is illustrated, but it may be configured such that a signal evaluation parameter is determined from a single medical concept.

When there are multiple words expressing characteristics of a symptom, such as "worsening during sleep, rest, and weight-bearing", and these words do not represent opposing relationships, two different ambiguities may be defined within one category (evaluation parameter). For example, in the case of "exacerbated during sleep, rest, and weight-bearing", two ambiguities, "constant vs. intermittent" and "during movement vs. during weight-bearing" are determined within a timing category.

Determination of the evaluation parameter is not limited to the method described above, but other methods may be used. For example, the determining function 153 can statistically extract evaluation parameters using a past interview content of patients. That is, the determining function 153 determines the evaluation parameter from the past interview content of patients with the same disease.

Figure 4B:
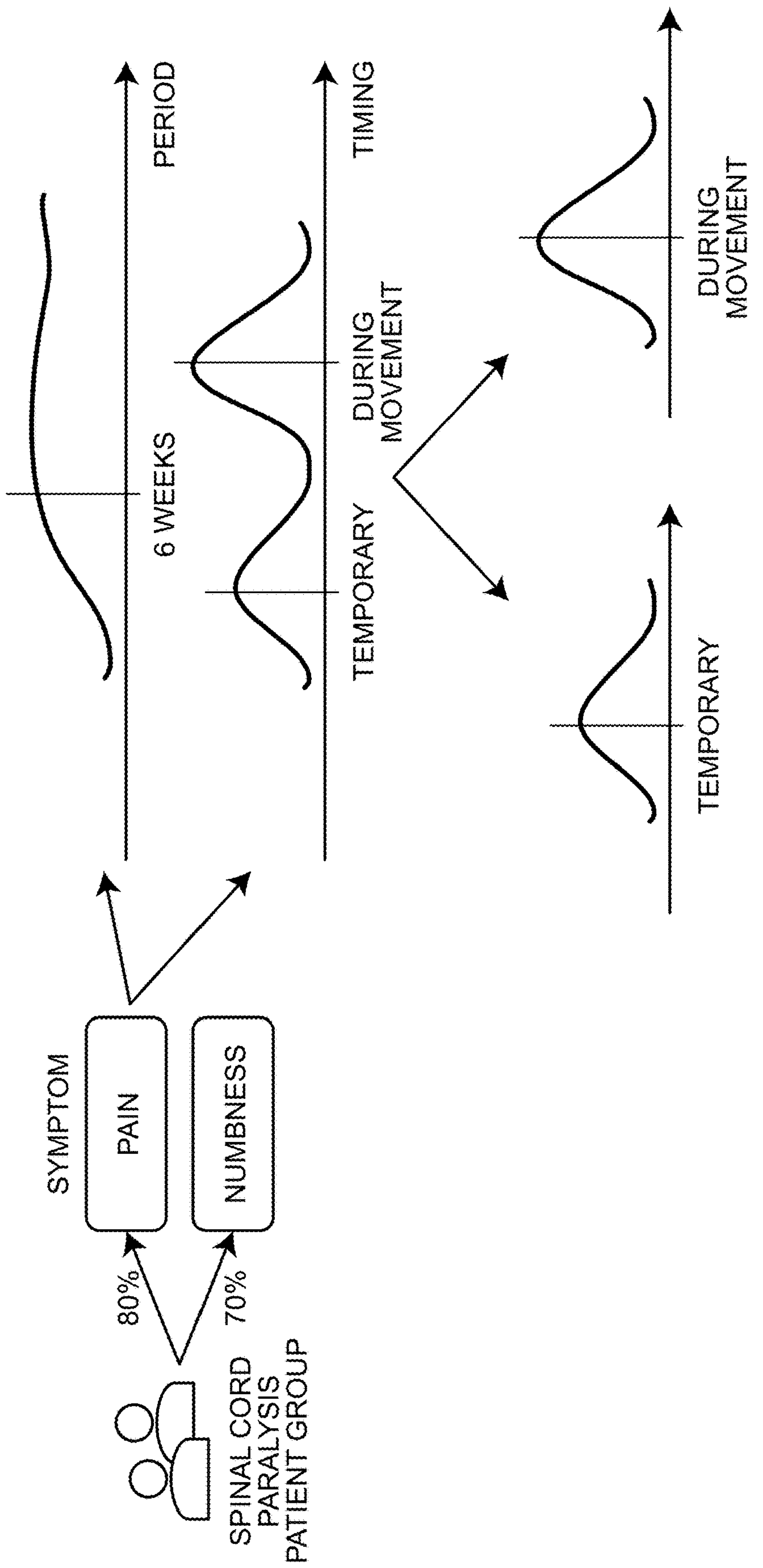
FIG. 4B is a diagram for explaining an example of determination processing of evaluation parameter according to the first embodiment.

FIG. 4B is a diagram for explaining an example of the determination processing of the evaluation parameter according to the first embodiment. FIG. 4B illustrates determination of an evaluation parameter based on an interview content of patients with spinal cord paralysis. For example, the determining function 153 extracts, as illustrated in FIG. 4B, "pain" reported by 80% of spinal cord paralysis patients and "numbness" reported by 70% as symptoms. Furthermore, the determining function 153 extracts a characteristic trend from an interview content of a patient, and determines evaluation parameters, such as "duration" and "timing". The determining function 153 determines two ambiguities, "constant vs. intermittent" and "during movement vs. during weight-bearing" within the timing category. As the method of extracting symptoms and the like from an interview content, for example, keyword extraction using language processing and topic analysis can be used.

Moreover, evaluation parameters are not limited to the categories of the symptoms described above, and other information may be used. For example, the medical concept includes an indicator or a score that indicates patient status. As one example, the Tokuhashi score that is used for prognostic prediction can also be considered the medical concept. The Tokuhashi score is scored by using "performance status: PS" containing ambiguity of "level of activity". Therefore, when the Tokuhashi score is used, PS is determined as the ambiguity. PS is set incrementally from a level in which "activity can be performed without problems" to a level in which "no movement is possible". That is, the determining function 153 determines the level of activity described above as the ambiguity of the Tokuhashi score. As the indicator indicating a patient status, the "activities of daily living (ADL)", which is an index to judge daily life activities may be used.

Figure 5:
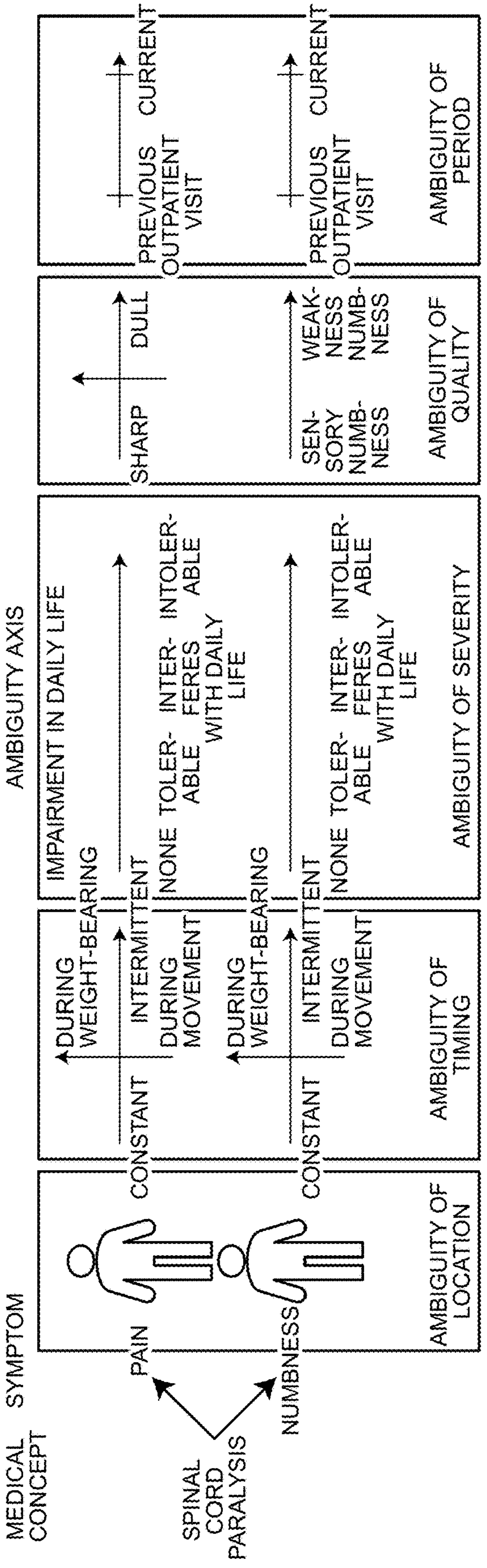
FIG. 5 is a diagram illustrating an example of the evaluation parameter determined by a determining function according to the first embodiment.

As described above, the determining function 153 determines the evaluation parameter for each medical concept identified by the identifying function 152. FIG. 5 is a diagram illustrating an example of the evaluation parameter determined by the determining function 153 according to the first embodiment. As illustrated in FIG. 5, for example, the determining function 153 identifies the evaluation parameters, "location", "timing", "severity", "quality", and "duration" for the symptoms, "pain" and "numbness" of the medical concept "spinal cord paralysis".

Each of the evaluation parameters determined by the determining function 153 contains ambiguity. For example, the evaluation parameter of "timing" contains ambiguities, "during weight-bearing vs. during movement" and "constant vs. intermittent" for both "pain" and "numbness". Moreover, the evaluation parameter of "severity" contains ambiguities ranging from "none" to "intolerable" in terms of impairment in daily life. Similarly, the respective evaluation parameters contain ambiguities for "pain" and "numbness".

As described above, the determining function 153 determines the evaluation parameter relating to the medical concept, "spinal cord paralysis". The determining function 153 performs processing similar to those described above with respect to all medical concepts that have been identified by the identifying function 152, and determines the respective evaluation parameters. For example, when the identifying function 152 has identified the medical concept, "pain due to bone metastasis", the determining function 153 determines an evaluation parameter relating to the medical concept, "pain due to bone metastasis".

Acquisition Processing of Chief Complaint and Medical Knowledge

As explained at step S103 in FIG. 2, the acquiring function 151 acquires medical knowledge relating to a chief complaint of a patient and a medical concept. Specifically, the acquiring function 151 acquires medical knowledge included in a document explaining the definition of the medical concept (including expressions, such as a table), and in information of cases and actual clinical information. For example, the acquiring function 151 acquires a medical knowledge from guidelines, literature information, expertise of physician, and a patient chart.

Figure 6:
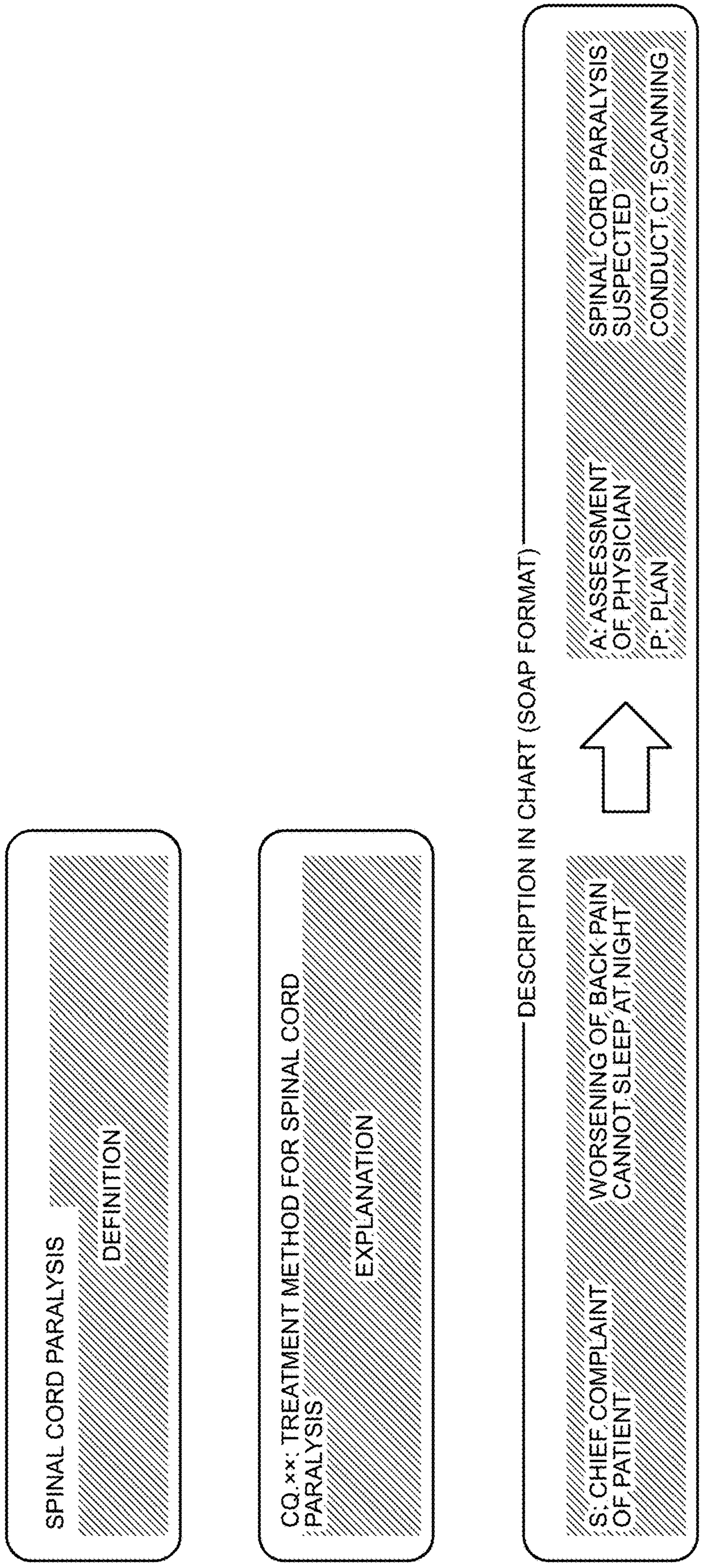
FIG. 6 is a diagram for explaining an example of acquisition of medical knowledge according to the first embodiment.

FIG. 6 is a diagram for explaining an example of acquisition of medical knowledge according to the first embodiment. For example, the acquiring function 151 acquires, as illustrated in an upper part of FIG. 1, guideline information and literature information from the data storage apparatus 2, and acquires definition statement defining the medical concept "spinal cord paralysis" by performing a search using the medical concept "spinal cord paralysis" on the acquired information. The acquiring function 151 then acquires characteristics of the medical concept "spinal cord paralysis".

Moreover, the acquiring function 151 acquires information of clinical question from the data storage apparatus 2 as illustrated in the drawing in a middle of FIG. 1, and acquires explanation described in the clinical question relating to the medical concept "spinal cord paralysis" by performing a search using the medical concept "spinal cord paralysis" on the acquired information. The acquiring function 151 then acquires characteristics of the medical concept "spinal cord paralysis" included in the explanation.

Furthermore, the acquiring function 151 acquires a patient chart from past diagnosis relating to the medical concept "spinal cord paralysis" from the data storage apparatus 2, and acquires medical knowledge from contents described in the acquired chart. For example, the acquiring function 151 acquires a chart relating to the medical concept "spinal cord paralysis" from description of "A: assessment of a physician" in the chart described in a soap format, and acquires medical knowledge from description of "S: chief complaint of patient" in the acquired chart.

When medical knowledge is acquired from a chart, to eliminate exceptional cases, trends and characteristics of interview contents regarding a subject disease state may be extracted using statistics and machine learning, and the extracted trends and characteristics may be acquired as medical knowledge. That is, the acquiring function 151 acquires trends and characteristics that have relatively high probabilities of being reported by a patient in the medical concept "spinal cord paralysis" as medical knowledge.

Moreover, the acquiring function 151 acquires a chief complaint data of a patient (current target patient) subject to resolving ambiguities. Specifically, the acquiring function 151 acquires a chief complaint of the patient (contents filled out by the patient on questionnaires and contents of the chart written by the physician, and the like), and a self-evaluation by the patient (responses to questionnaires for disease differentiation and a subjective pain score, such as numerical rating score (NRS)).

Figure 7:
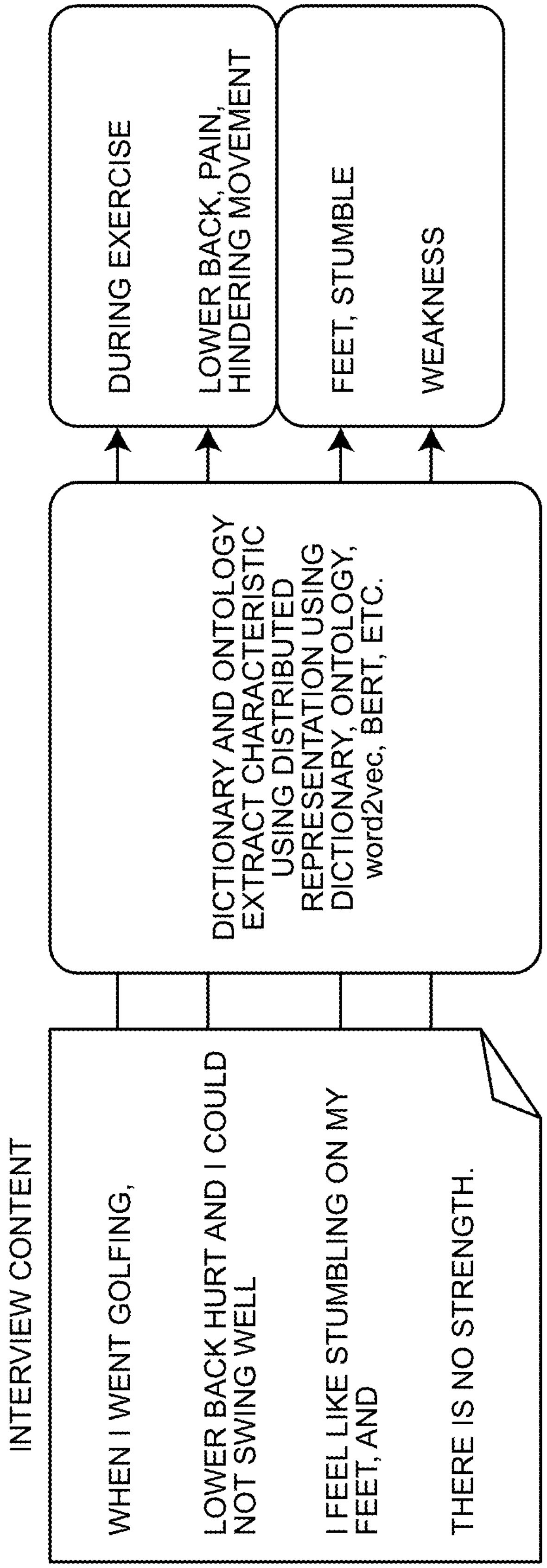
FIG. 7 is a diagram for explaining an example of feature extraction according to the first embodiment.

The acquiring function 151 then acquires trends and characteristics included in the acquired chief complaint data. FIG. 7 is a diagram for explaining an example of characteristic extraction according to the first embodiment. FIG. 7 illustrates an example of characteristic extraction from interview contents. For example, the acquiring function 151 extracts characteristics from the interview contents, as illustrated in FIG. 7, by applying distributed representations using dictionaries, ontology, word2vec, or BERT to the interview contents.

For example, the acquiring function 151 acquires a characteristic "during exercise" from "when I went golfing" included in the interview contents, and acquires characteristics "lower back, pain, hindering movement" from "lower back hurt and I could not swing well" included in the interview contents. Moreover, the acquiring function 151 acquires characteristics "feet, stumble" from "feel like stumbling on my feet" included in the interview contents, and acquires the characteristic "weakness" from "there is no strength" included in the interview contents.

Mapping Processing

As explained at step S104 in FIG. 2, the mapping function 154 maps the first range based on chief complaint data and the second range based on medical knowledge on a space based on the evaluation parameters. Specifically, the mapping function 154 determines a range of ambiguity contained in a characteristic of the chief complaint data (evaluation by the patient) acquired by the acquiring function 151 and a range of ambiguity contained in a characteristic in the medical knowledge (evaluation based on the medical knowledge) for each evaluation parameter.

When mapping the range of a characteristic relating to numerical continuous values, such as age, duration, and score, the mapping function 154 maps the range with respect to a coordinate space indicating numerical values. For example, as indicated by the ambiguity of duration in FIG. 5, the mapping function 154 uses a coordinate space representing "previous outpatient visit" and "current".

Furthermore, when mapping a range of a word (characteristic) expressing a quality or severity of a symptom, the mapping function 154 maps a range with respect to a coordinate space in which antonyms of words become opposing poles on the axis. That is, the mapping function 154 uses a coordinate space in which evaluations in opposite relationships are shown at both ends of the coordinate axis. For example, as indicated in ambiguities in timing, severity, and quality illustrated in FIG. 5, the mapping function 154 uses a coordinate space in which antonyms are indicated at both ends.

Components of axis and coordinates of each component (position on the coordinate space) can be determined by rule-based approach using dictionaries or ontology, principal component analysis, or manual operation by a physician. Moreover, relative coordinates of each component may also be calculated using word vector representations obtained by natural language processing, such as word2vec.

Furthermore, when mapping a range of a word (characteristic) containing a discrete value, such as location information, but also positional coordinates, the mapping function 154 maps a range with respect to a human body diagram or a knowledge graph. That is, the mapping function 154 uses a coordinate space indicating a position in a patient as a space based on the evaluation parameters. For example, as ambiguity of location in FIG. 5, the mapping function 154 uses a coordinate space represented by a human body diagram.

The mapping function 154 maps the first range based on the chief complaint data and the second range based on the medical knowledge with respect to the coordinate space described above. Specifically, the mapping function 154 maps the first range and the second range on the space based on the evaluation parameters for each evaluation parameter. For example, the mapping function 154 determines the first range based on the range statistically determined in a medical concept same as the medical concept of the patient. For example, the mapping function 154 determines the first range based on the chief complaint of the patient using a rule-based approach, machine learning, normal distribution, and the like using dictionaries or ontologies.

Figure 8:
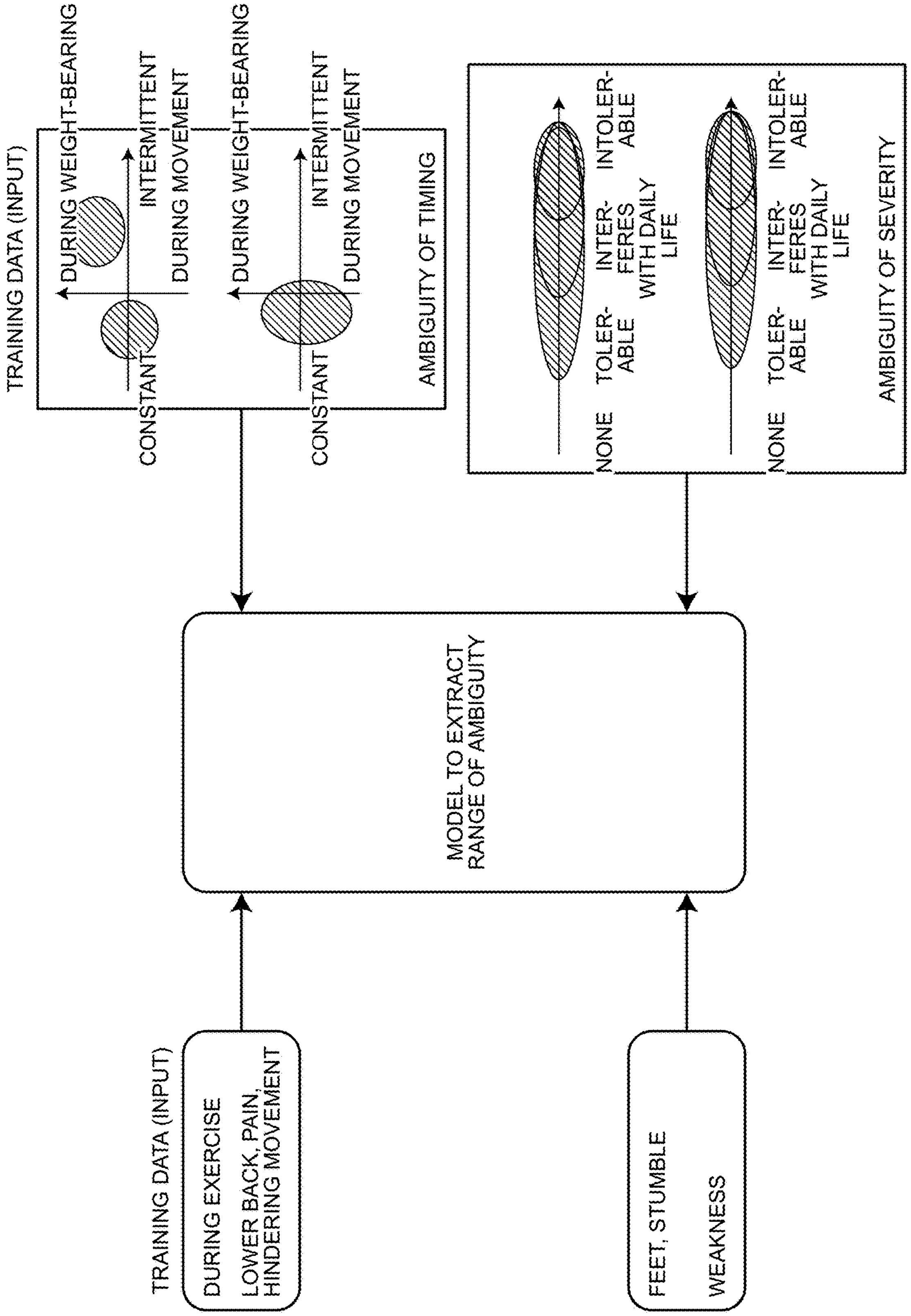
FIG. 8 is a diagram for explaining construction of a trained model to determine a first range according to the first embodiment.

Hereinafter, an example of determining a range using machine learning will be explained. FIG. 8 is a diagram for explaining construction of a trained model to determine the first range according to the first embodiment. For example, as illustrated in FIG. 8, the trained model to extract a range of ambiguity is constructed by training a characteristic acquired from past chief complaint data of a patient and a range of ambiguity predefined for each characteristic of medical knowledge relating to a medical concept (training data) as training data.

The range of ambiguity is a range that can be of each characteristic with respect to the coordinate space for each category such as timing and severity. For example, a range of timing for "pain" in a patient with spinal cord paralysis is "constant", and a range of timing for "numbness" is often "constant", but some include "occasional".

For example, a trained model to extract a range of ambiguity relating to "spinal cord paralysis" is constructed by training a characteristic included in a chief complaint of a patient that has been diagnosed as "spinal cord paralysis" and a range predefined for each characteristic of medical knowledge relating to "spinal cord paralysis" (training data) as training data. A range of ambiguity of each characteristic of medical knowledge relating to a medical concept is defined in advance, for example, based on guidelines and literature information. Moreover, a range of ambiguity of each characteristic of medical knowledge relating to a medical concept may be assigned with a grade based on a confidence level as indicated in ambiguity of severity in FIG. 8.

Figure 9:
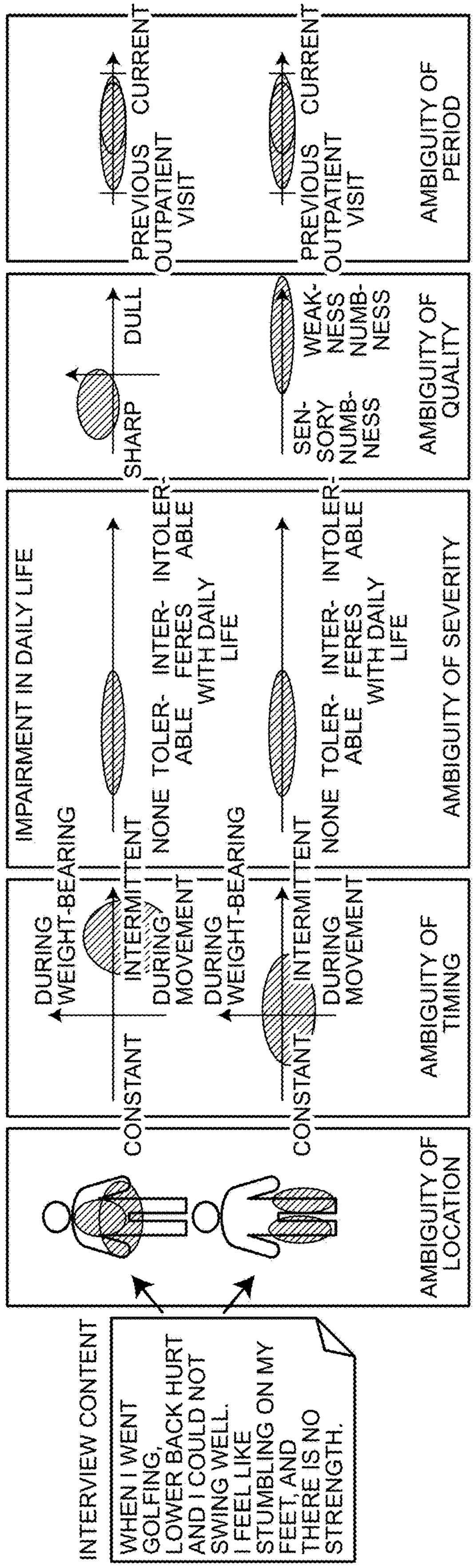
FIG. 9 is a diagram illustrating an example of mapping of the first range according to the first embodiment.

The mapping function 154 acquires the first range by inputting a characteristic acquired from chief complaint data of a patient (current target patient) subject to resolving ambiguities to the trained model to extract a range of ambiguity. FIG. 9 is a diagram illustrating an example of mapping of the first range according to the first embodiment. For example, the mapping function 154 acquires a range of ambiguity illustrated in FIG. 9 by inputting a characteristic acquired from chief complaint data of a current target patient by the acquiring function 151 to the trained model. That is, the mapping function 154 determines a range indicating the ambiguity contained in a complaint of the patient (evaluation) for the evaluation parameter to evaluate the medical concept "spinal cord paralysis".

Moreover, the mapping function 154 maps the range of ambiguity of each characteristic of the medical knowledge relating to the medical concept on a coordinate space based on the evaluation parameter. The range of ambiguity of each characteristic of medical knowledge relating to the medical concept is defined in advance as described above. Therefore, the mapping function 154 acquires a range of ambiguity predefined for a characteristic acquired from medical knowledge by the acquiring function 151.

Figure 10:
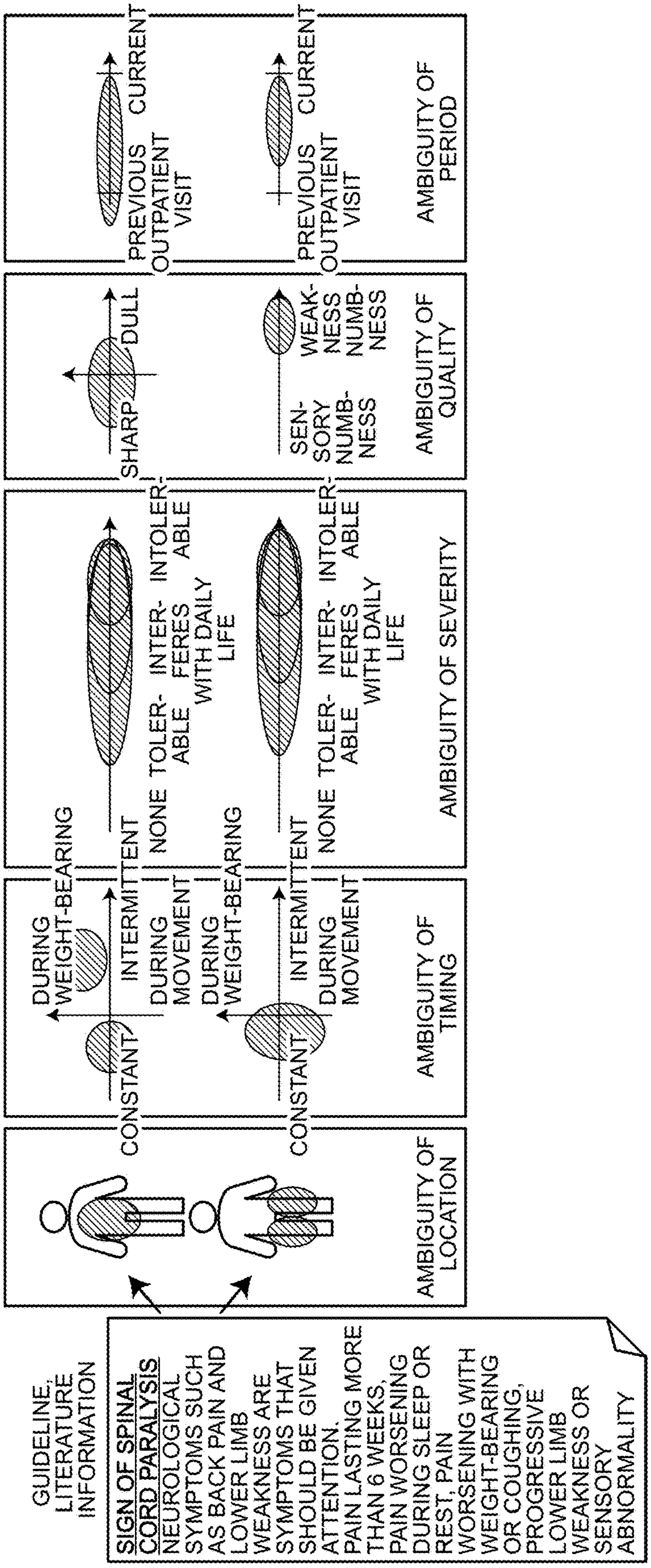
FIG. 10 is a diagram illustrating an example of mapping of a second range according to the first embodiment.

FIG. 10 is a diagram illustrating an example of mapping of the second range according to the first embodiment. For example, the mapping function 154 acquires a range of ambiguity of a characteristic in each category based on characteristics of medical knowledge "sign of spinal cord paralysis" acquired from guidelines and literature information as illustrated in FIG. 10. That is, the mapping function 154 determines a range of characteristic that can be complained by a patient of spinal cord paralysis for characteristics in each category.

Calculation Processing of Relevance

As explained at step S105 in FIG. 2, the calculating function 155 calculates relevance between chief complaint data of a patient and medical knowledge based on the first range and the second range. Specifically, the calculating function 155 calculates the relevance between the chief complaint data of the patient and medical knowledge based on the range of ambiguity based on the chief complaint of the patient (range indicating ambiguity contained in a complaint (evaluation) reported by the patient) and the range of ambiguity based on the medical knowledge (range of a characteristic that can be reported by the patient having the medical concept).

For example, the calculating function 155 calculates relevance based on an area in which the first range and the second range overlap each other. As one example, the calculating function 155 calculates a degree of match between the chief complaint data of the patient and the medical knowledge based on an area in which the range of ambiguity based on the chief complaint of the patient and the range of ambiguity based on the medical knowledge overlap each other.

Figure 11:
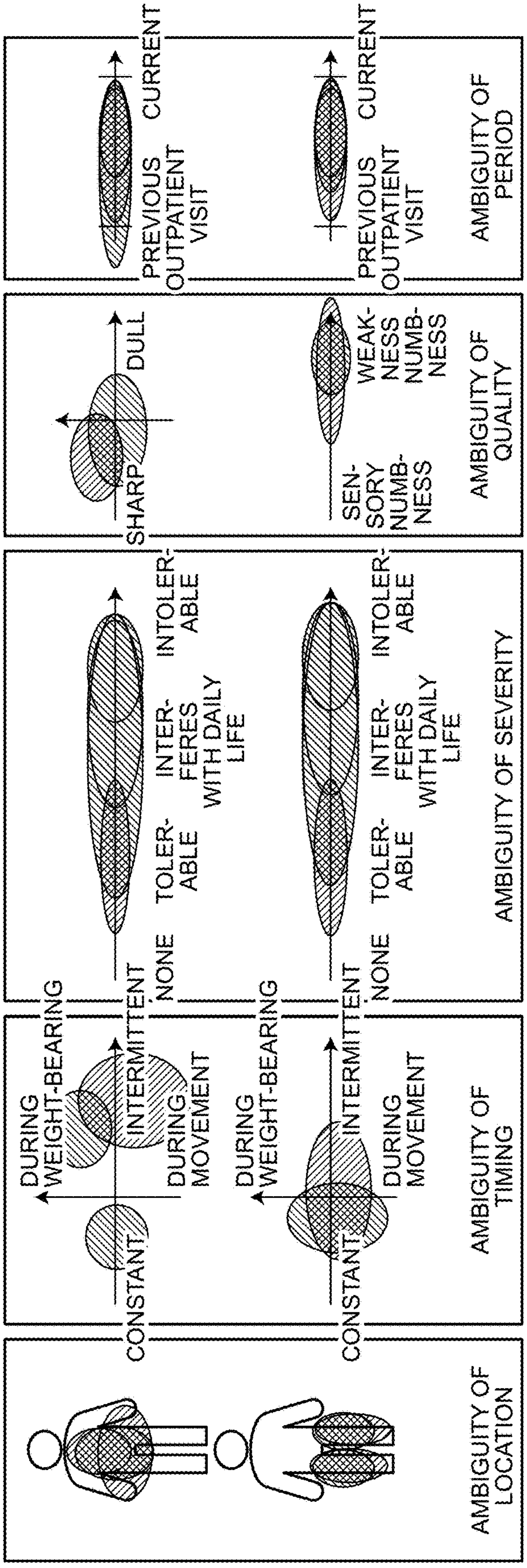
FIG. 11 is a diagram for explaining calculation of relevance according to the first embodiment.

FIG. 11 is a diagram for explaining calculation of the relevance according to the first embodiment. FIG. 11 illustrates a diagram in which the range of ambiguity contained in the complaint (evaluation) by the patient illustrated in FIG. 9 and the range of ambiguity based on the medical knowledge illustrated in FIG. 10 are overlapped. For example, the calculating function 155 calculates an area in which the ranges overlap in FIG. 11 for each category, and calculates a degree of match between the chief complaint and the medical knowledge based on the calculated area. As one example, the calculating function 155 calculates the total sum of the calculated areas as the degree of match.

The calculating function 155 can assign weights to each characteristic, such as assigning heavier weights to key characteristic. For example, a characteristic for which ambiguity is to be resolved to discriminate from other medical concepts (medical concepts other than spinal cord paralysis) is assigned to a heavy weight. Alternatively, a key characteristic may be extracted by statistical processing or machine learning with respect to a medical concept, and a heavier weight may be assigned to the extracted characteristic. Information related to weighting is set in advance, and is stored in the storage circuitry 14. That is, when weighting is performed, the calculating function 155 reads out information related to weighting from the storage circuitry 14 to use it.

For example, the calculating function 155 calculates a degree of match by using a following equation. The following equation indicates an equation for performing weighting, but weighting may be omitted.

$$\Sigma\_\text{all ranges of ambiguity}(\text{weight of characteristic} \times \text{overlapping area}) = \text{degree of match}$$

The relevance between a chief complaint and medical knowledge is not limited to be acquired by the method using areas as described above, but other methods may be used. For example, the calculating function 155 can calculate the relevance between a chief complaint and medical knowledge by calculating a similarity between the first range (range of ambiguity contained in the complaint (evaluation) by the patient) and the second range (range of ambiguity based on the medical knowledge) by calculating a cos (cosine) similarity using vector representation. Furthermore, the calculating function 155 can calculate the relevance between a chief complaint and medical knowledge also by performing hypotheses testing between the first range (range of ambiguity contained in the complaint (evaluation) by the patient) and the second range (range of ambiguity based on the medical knowledge).

Moreover, calculation method of the relevance using overlapped area is not limited to the methods described above, but a confidence level may be used in addition to area when a range of ambiguity is evaluated by confidence level. In such a case, the calculating function 155 can calculate the degree of match including the confidence level by adding up weights, assigning heavier weights to coordinates with high confidence levels in an overlapping range.

As described above, the calculating function 155 calculates the degree of match between a chief complaint of a patient and medical knowledge for each medical concept.

Display Processing of Information

As explained at step S106 in FIG. 2, the display control function 156 displays information based on the relevance. For example, the display control function 156 displays the degree of match calculated by the calculating function 155 on the display 13.

Figure 12:
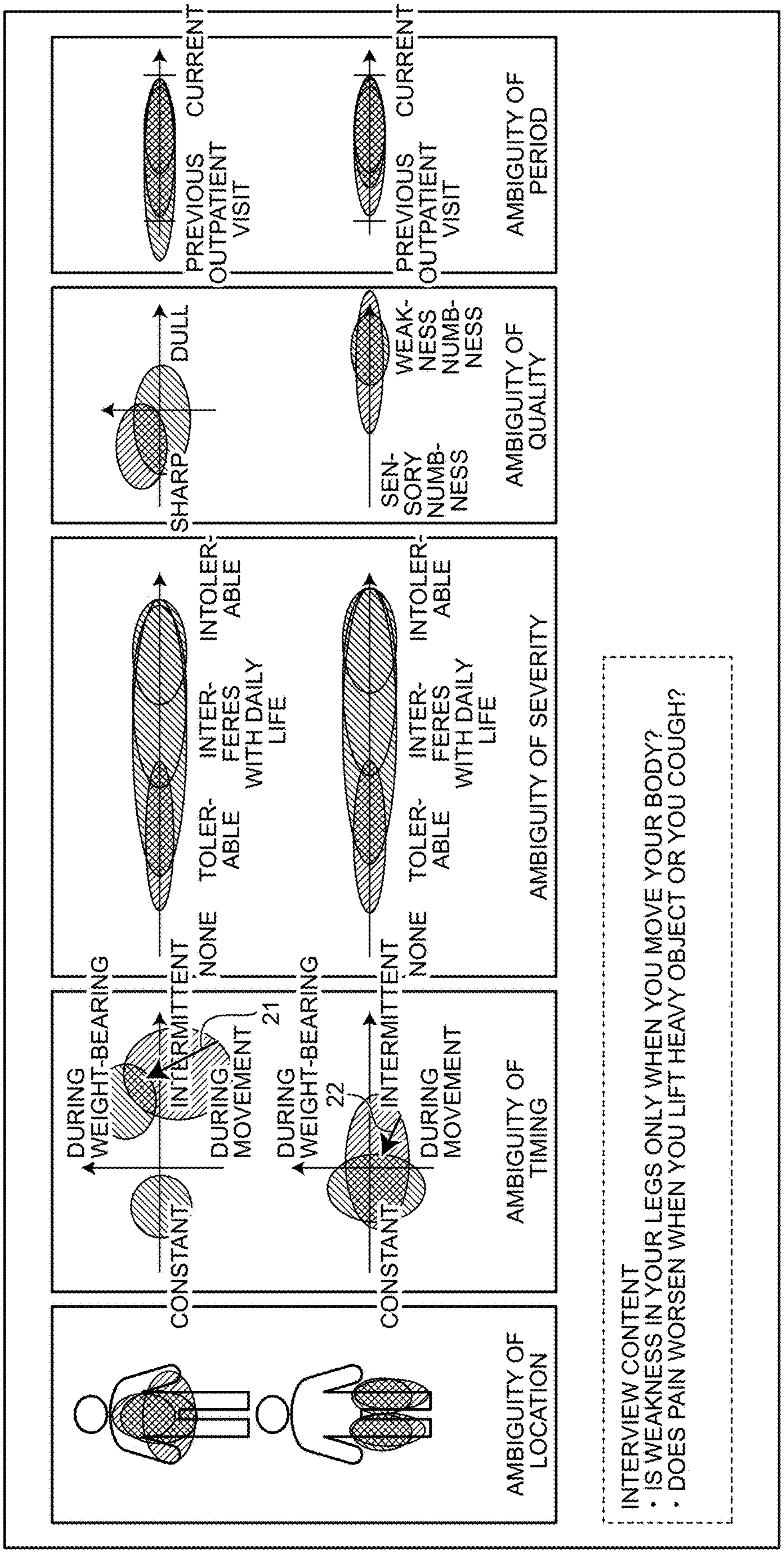
FIG. 12 is a diagram illustrating an example of display information according to the first embodiment.

Moreover, for example, the display control function 156 can display information in which the first range and the second range are mapped on the space based on the evaluation parameters. FIG. 12 is a diagram illustrating an example of display information according to the first embodiment. For example, the display control function 156 displays information in which a range of ambiguity contained in a complaint by a patient (evaluation) and a range of ambiguity based on medical knowledge are overlayed for the medical concept "spinal cord paralysis" on the display 13.

The display control function 156 can display directions to resolve ambiguity in a characteristic in each category as indicated by arrows 21, 22 in FIG. 12. Thus, a physician can resolve the ambiguity by inquiring in more detail about the timing of "pain" and "numbness" by referring to the arrows 21 and 22.

Moreover, for example, the display control function 156 displays interview contents to the patient based on relevance. As one example, the display control function 156 displays the interview contents, "Is weakness in your legs only when you move your body?" and "Does pain worsen when you lift heavy object or you cough?" as illustrated in FIG. 12. The interview contents are set in advance for each direction to resolve ambiguity and stored in the storage circuitry 14. That is, the display control function 156 reads out the interview contents based on the directions of the arrows 21 and 22, to display on the display 13.

As described above, according to the first embodiment, the identifying function 152 identifies a medical concept relating to a patient. The determining function 153 determines the evaluation parameter relating to the medical concept. The acquiring function 151 acquires chief complaint data of a patient and medical knowledge relating to a medical concept. The mapping function 154 maps the first range based on the chief complaint and the second range based on the medical knowledge. Therefore, the medical information processing apparatus 1 according to the first embodiment can compare the first range based on the chief complaint data and the second range based on the medical knowledge, and by conducting an interview based on a comparison result, the efficiency of diagnosis can be improved. Moreover, by conducting an interview based on the comparison result, it becomes possible to suppress occurrence of overlooking of signs of a serious disease or an adverse event.

Furthermore, according to the first embodiment, the evaluation parameters are parameters relating to medical concepts and containing ambiguities. Moreover, the determining function 153 determines a parameter with an evaluation that includes ambiguity as the evaluation parameter out of parameters to evaluate a medical concept of a patient. Therefore, the medical information processing apparatus 1 according to the first embodiment enables to conduct an interview so as to resolve ambiguity contained in chief complaint data, and to improve the efficiency of diagnosis.

Moreover, according to the first embodiment, the mapping function 154 determines the first range on a space based on evaluation parameters based on an evaluation relating to a medical concept included in a chief complaint, and determines the second range on a space based on evaluation parameters based an evaluation relating to the medical concept included in medical knowledge. Therefore, the medical information processing apparatus 1 according to the first embodiment can compare a range based on the evaluation by the patient and a range based on the medical knowledge, and enables an interview based on a comparison result.

Furthermore, according to the first embodiment, the mapping function 154 determines the first range based on a range statistically determined for a medical concept same as a medical concept of a patient. Therefore, the medical information processing apparatus 1 according to the first embodiment enables to determine a range based on a chief complaint of a patient highly accurately.

Moreover, according to the first embodiment, the mapping function 154 uses a coordinate space in which evaluations in opposite relationships are shown at both ends of the coordinate axis is used as the space based on the evaluation parameters. Furthermore, the mapping function 154 uses a coordinate space indicating a location in a patient as the space based on the evaluation parameters. Therefore, the medical information processing apparatus 1 according to the first embodiment enables to represent the evaluation parameter appropriately.

Moreover, according to the first embodiment, a medical concept is information relating to a disease of the patient. Therefore, the medical information processing apparatus 1 according to the first embodiment enables to conduct an appropriate interview about a disease of a patient.

Furthermore, according to the first embodiment, the determining function 153 determines multiple kinds of evaluation parameters relating to a medical concept. The mapping function 154 maps the first range and the second range on the space based on the evaluation parameters. Therefore, the medical information processing apparatus 1 according to the first embodiment enables to perform processing for multiple evaluation parameters.

Moreover, according to the first embodiment, the calculating function 155 calculates relevance between a chief complaint and medical knowledge based on the first range and the second range. Therefore, the medical information processing apparatus 1 according to the first embodiment enables comparison between the chief complaint of a patient and the medical knowledge.

Furthermore, according to the first embodiment, the calculating function 155 calculates relevance based on an area in which the first range and the second range overlap each other. Therefore, the medical information processing apparatus 1 according to the first embodiment enables to calculate relevance between a chief complaint of a patient and medical knowledge easily.

Moreover, according to the first embodiment, the display control function 156 displays information based on the relevance. Therefore, the medical information processing apparatus 1 according to the first embodiment enables to provide information on the relevance to a physician.

Furthermore, according to the first embodiment, the display control function 156 displays information in which the first range and the second range are mapped on the space based on the evaluation parameter. Therefore, the medical information processing apparatus 1 according to the first embodiment enables to provide easily observable information on the relevance to a physician.

Moreover, according to the first embodiment, the display control function 156 displays interview contents to a patient based on the relevance. Therefore, the medical information processing apparatus 1 according to the first embodiment enables to provide appropriate information for the interview to a physician.

Second Embodiment

In the first embodiment described above, a case in which an evaluation parameter is determined after identifying a target medical concept has been explained. In a second embodiment, a case in which an evaluation parameter is determined based on a chief complaint of a patient, and the first range is mapped for the determined evaluation parameter, and a medical concept is identified based on a result of mapping will be explained. For example, there is a case in which a physician wishes to search for a medical concept having higher relevance, considering ambiguity contained in chief complaint data of a patient. In the second embodiment, processing for such a case will be explained. The medical information processing apparatus 1 according to the second embodiment differs in processing of the identifying function 152 and the determining function 153 from those in the first embodiment. Hereinafter, these will be explained mainly.

The determining function 153 according to the second embodiment determines an evaluation parameter based on a characteristic of a chief complaint acquired by the acquiring function 151. For example, the determining function 153 determines a category and a characteristic for which a range of ambiguity is mapped, based on characteristics of the chief complaint, "during exercise", "lower back, pain, inhibition of movement", "feet, stumbling", and "weakness".

The mapping function 154 according to the second embodiment maps the first range based on the chief complaint on a coordinate space of the evaluation parameter (category) determined by the determining function 153 based on the characteristics of the chief complaint acquired by the acquiring function 151 similarly to the first embodiment.

The identifying function 152 according to the second embodiment identifies a medical concept based on a mapping result by the mapping function 154. Specifically, the identifying function 152 identifies a medical concept having a range relating to the first range mapped by the mapping function 154 as a target medical concept.

In such a case, for example, the calculating function 155 respectively calculates a degree of match between the first range mapped by the mapping function 154 and a range (second range) of ambiguity of each medical knowledge relating to the medical concept stored in the storage circuitry 14. The identifying function 152 identifies a medical concept to be a target based on the degree of match calculated by the calculating function 155.

For example, the identifying function 152 extracts all of medical concepts having a possibility of match, and identifies the extracted medical concept as the target medical concept. Moreover, for example, the identifying function 152 identifies a medical concept having the highest calculated degree of match as the target medical concept.

The evaluation parameter based on the chief complaint may be determined by the determining function 153 as described above, but it may be designated by a physician. For example, it may be selected by a physician from among evaluation parameters determined by the determining function 153.

According to the second embodiment, a medical concept considering ambiguity contained in a chief complaint of a patient can be identified. That is, not only a search considering a meaning of a word (synonyms and the like) and an ontological relationship, but also a search based on ambiguity inherent in the word is possible.

Third Embodiment

In the first embodiment described above, a case in which ambiguities in chief complaint data of a patient and medical knowledge are compared has been explained. In the third embodiment, a case in which ambiguities in perception of a user of a word are compared will be explained. For example, even with the same expression, discrepancies can arise when there are differences in perception between a speaker and a listener (for example, between a patient and a healthcare provider, or among healthcare providers). Therefore, in the third embodiment, by comparing ambiguities of word among users to resolve discrepancies. The medical information processing apparatus 1 according to the third embodiment differs in processing of the acquiring function 151, the calculating function 155, and the display control function 156 from those in the first embodiment. Hereinafter, these will be explained mainly.

The acquiring function 151 according to the third embodiment acquires a statement made by a user and acquires a characteristic related to a specific disease state included in the acquired statement. For example, the acquiring function 151 acquires statements of a patient and a physician at an interview in real time, and acquires a characteristic related to a specific disease state included in the acquired statements. As one example, the medical information processing apparatus 1 includes an input interface 12 and a microphone, and the acquiring function 151 acquires characteristics related to the specific disease state included in the statements of the patient and the physician acquired by the microphone. The characteristics related to the specific disease state included in the statements of the patient and the physician are acquired by a language processing technique.

The mapping function 154 according to the third embodiment respectively maps a range of ambiguity based on the characteristic related to the specific disease state stated by the patient and a range of ambiguity based on the characteristic related to the specific disease state stated by the physician. Evaluation parameters are set in advance for each specific disease state.

The calculating function 155 according to the third embodiment calculates a degree of match based on the ranges mapped by the mapping function 154. For example, the calculating function 155 calculates a degree of match between the range of ambiguity based on the characteristic related to the specific disease state stated by the patient and the range of ambiguity based on the characteristic related to the specific disease state stated by the physician.

The display control function 156 according to the third embodiment displays information based on the degree of match calculated by the calculating function 155. For example, the display control function 156 displays information indicating occurrence of discrepancies on the display 13 when the degree of match calculated by the calculating function 155 is lower than a threshold.

Note that a case in which ambiguities of perception of uses of a word are compared is not limited to the one described above. For example, among healthcare providers, it is possible to compare ambiguities from descriptions in a chart. For example, the acquiring function 151 acquires a characteristic of a word related to a specific medical concept of respective healthcare providers from the word described in the chart. The mapping function 154 respectively maps ranges of ambiguities of the respective healthcare providers based on the acquired characteristic of the word.

The display control function 156 presents a mapping result to the respective healthcare providers. Thus, discrepancies in perception can be grasped among the healthcare providers. For example, when an order is issued, by presenting a range of ambiguity of an issuing physician, a receiving physician can act to resolve discrepancies by comparing it with his/her own understanding.

According to the third embodiment, by absorbing discrepancies in symptom between a patient and a physician during an interview, or discrepancies between physicians in a request to other treatment departments, such as a test order, more accurate information transmission and treatment are facilitated.

Other Embodiments

In the embodiments described above, a case in which processing based on a range of ambiguity is performed in the medical information processing apparatus 1 has been explained. However, the embodiments are not limited thereto, and other devices can use information of a range of ambiguity acquired by the medical information processing apparatus 1.

For example, when a trained model or an expert system is constructed using chief complaint data of a patient, by inputting a range of ambiguity acquired by the medical information processing apparatus 1, a trained model or an expert system that is capable of providing a broad suggestion considering ambiguities can be constructed.

For example, when an answer containing a high level of ambiguity is input, the confidence level of a suggestion provided by the trained model or expert system decreases. Because it is possible to determine whether the ambiguity is high (for example, whether a mapped range is broad, or the like) by inputting a range of ambiguity acquired by the medical information processing apparatus 1, it is possible to present which ambiguity should be resolved to improve the confidence level.

Moreover, for example, by using the range of ambiguity obtained by the medical information processing device 1 in fuzzy inference to infer ambiguity or inaccuracy, it becomes possible to provide a confidence level for an inference result in fuzzy inference.

In the embodiment described above, an example in which an acquiring unit, an identifying unit, a determining unit, a mapping unit, a calculating unit, and a display control unit in the present specification are implemented by the acquiring function, the identifying function, the determining function, the mapping function, the calculating function, and the display control function has been explained, but embodiments are not limited thereto. For example, the acquiring unit, the identifying unit, the determining unit, the mapping unit, the calculating unit, and the display control unit in the present specification may be configured to be implemented by hardware only, software only, or a combination of hardware and software, other than being implemented by the acquiring function, the identifying function, the determining function, the mapping function, the calculating function, and the display control function described in the embodiments.

Moreover, a term "processor" used in the explanation of the embodiments described above signifies a circuit, such as a central processing unit (CPU), a graphical processing unit (GPU), an application specific integrated circuit (ASIC), a programmable logic device (for example, simple programmable logic device (SPLD), complex programmable logic device (CPLD)), and a field programmable gate array (FPGA). Instead of storing a program in the storage circuit, it may be configured to directly install a program in a circuit of the processor. In this case, the processor reads and executes the program installed in the circuit, to implement the function. Furthermore, the respective processors of the present embodiment are not limited to be configured as a single circuit for each processor, but may be configured by combining plural pieces of independent circuit as one processor, to implement its function.

A medical information processing program executed by a processor is installed in advance in a read only memory (ROM), a storage circuit, or the like to be provided. The medical information processing program may also be provided being stored in a non-transitory computer-readable storage medium that can be read by a computer, such as a compact disk (CD)-ROM, a flexible disk (FD), a compact disk recordable (CD-R), a digital versatile disk (DVD), in a file of a format that can be installed in or executed by a computer. Moreover, this medical information processing program may be stored in a computer connected to a network, such as the Internet, and may be provided or distributed by being downloaded through the network. For example, this medical information processing program is constituted of modules including the respective processing functions described above. As actual hardware, the medical image-processing program is read from the storage medium, such as a ROM, to be executed by a CPU, and the respective modules are loaded on a main storage device, and are generated on the main storage device.

Furthermore, in the embodiments and a modification described above, the respective components of the respective devices illustrated are of functional concept, and it is not necessarily required to be configured physically as illustrated. That is, specific forms of distribution and integration of the respective devices are not limited to the ones illustrated, and all or some thereof can be configured to be distributed or integrated functionally or physically in arbitrary units according to various kinds of loads, usage conditions, and the like.

Moreover, as for the respective processing functions performed in the respective devices, all or some arbitrary processing are implemented by a CPU and a program analyzed and executed by the CPU, or implemented as hardware by wired logic.

Furthermore, out of the respective processing explained in the above embodiments and modifications, all or some of processing explained to be performed automatically can also be performed manually, or all or some of processing explained to be performed manually can also be performed automatically by a publicly-known method. Besides, the processing procedure, the control procedure, the specific names, and the information including various kinds of data and parameters described in the above document or in the drawings can be arbitrarily changed, unless otherwise specified.

According to at least one of the embodiments explained above, it is possible to improve the efficiency of diagnosis.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical information processing apparatus comprising:

processing circuitry configured to identify information of a disease relating to a patient, determine a plurality of evaluation parameters for evaluating the disease related to the patient, generate a plurality of coordinate spaces corresponding to the plurality of evaluation parameters respectively, acquire chief complaint data of the patient and medical knowledge relating to the disease, determine, for each coordinate space, a first range indicating an ambiguity of characteristic contained in the chief complaint data within the coordinate space by inputting the characteristic contained in the chief complaint data into a trained model, the trained model that uses a characteristic contained in chief complaint data as input and outputs a range corresponding to an ambiguity in a coordinate space of evaluation parameters, determine, for each coordinate space, a second range indicating an ambiguity of characteristic contained in the medical knowledge within the coordinate space, calculate, for each coordinate space, an area in where the first range and the second range overlap each other on the coordinate space, calculate a degree of match between the chief complaint data and the medical knowledge based on the calculated area, and cause a display to display the degree of match between the chief complaint data and the medical knowledge.

2. The medical information processing apparatus according to claim 1, wherein each of the plurality of evaluation parameters is a parameter that contains ambiguity.

3. The medical information processing apparatus according to claim 1, wherein the processing circuitry is further configured to determine the first range on the coordinate space based on the evaluation parameter based on evaluation relating to the characteristic included in the chief complaint data, and determine the second range on the coordinate space based on the evaluation parameter based on evaluation relating to the characteristic included in the medical knowledge.

4. The medical information processing apparatus according to claim 3, wherein the processing circuitry is further configured to determine the first range based on a range statistically determined in a disease same as the disease relating to the patient.

5. The medical information processing apparatus according to claim 3, wherein the processing circuitry is further configured to use, as the coordinate space based on the evaluation parameter, a coordinate space in which evaluations in opposite relationships in the evaluation are shown at both ends of a coordinate axis.

6. The medical information processing apparatus according to claim 3, wherein the processing circuitry is further configured to use, as the coordinate space based on the evaluation parameter, a coordinate space indicating a location in the patient.

7. The medical information processing apparatus according to claim 1, wherein the processing circuitry is further configured to cause a display to display information based on the degree of match between the chief complaint data and the medical knowledge.

8. The medical information processing apparatus according to claim 1, wherein the processing circuitry is further configured to cause the display to display information in which the first range and the second range are mapped on the coordinate space on corresponding to the evaluation parameter.

9. The medical information processing apparatus according to claim 1, wherein the processing circuitry is further configured to cause the display to display an interview content to the patient based on the degree of match between the chief complaint data and the medical knowledge.

10. The medical information processing apparatus according to claim 1, wherein the processing circuitry is further configured to set a weight for characteristic, and calculate the degree of match based on the weight and the area in where the first range and the second range overlap each other.

11. The medical information processing apparatus according to claim 10, wherein the weight is set higher for a characteristic that should resolve ambiguity.

12. The medical information processing apparatus according to claim 1, wherein the processing circuitry is further configured to calculate a cosine similarity between a vector indicating the first range and a vector indicating the second range as the degree of match between the chief complaint data and the medical knowledge.

13. A medical information processing method comprising:

identifying information of a disease relating to a patient;

determining a plurality of evaluation parameters for evaluating the disease related to the patient;

generating a plurality of coordinate spaces corresponding to the plurality of evaluation parameters respectively, acquiring chief complaint data of the patient and medical knowledge relating to the disease;

determining, for each coordinate space, a first range indicating an ambiguity of characteristic contained in the chief complaint data within the coordinate space by inputting the characteristic contained in the chief complaint data into a trained model, the trained model that uses a characteristic contained in chief complaint data as input and outputs a range corresponding to an ambiguity in a coordinate space of evaluation parameters;

determining, for each coordinate space, a second range indicating an ambiguity of characteristic contained in the medical knowledge within the coordinate space;

calculating, for each coordinate space, an area in where the first range and the second range overlap each other on the coordinate space;

calculating a degree of match between the chief complaint data and the medical knowledge based on the calculated area, and causing a display to display the degree of match between the chief complaint data and the medical knowledge.

14. A storage medium that stores, in a non-transitory manner, a program causing a computer to execute respective processing, the processing comprising:

identifying information of a disease relating to a patient;

determining a plurality of evaluation parameters for evaluating the disease related to the patient;

generating a plurality of coordinate spaces corresponding to the plurality of evaluation parameters respectively:

acquiring chief complaint data of the patient and medical knowledge relating to the disease;

determining, for each coordinate space, a first range indicating an ambiguity of characteristic contained in the chief complaint data within the coordinate space by inputting the characteristic contained in the chief complaint data into a trained model, the trained model that uses a characteristic contained in chief complaint data as input and outputs a range corresponding to an ambiguity in a coordinate space of evaluation parameters;

determining, for each coordinate space, a second range indicating an ambiguity of characteristic contained in the medical knowledge within the coordinate space;

calculating, for each coordinate space, an area in where the first range and the second range overlap each other on the coordinate space;

calculating a degree of match between the chief complaint data and the medical knowledge based on the calculated area, and causing a display to display the degree of match between the chief complaint data and the medical knowledge.

* * * * *